United States Patent [19]
Yoslow et al.

[11] 3,991,745
[45] Nov. 16, 1976

[54] CURVATURE MEASUREMENT DEVICE

[75] Inventors: Wilfred Yoslow, Brooklyn; Alvin Bicker, East Setauket; Mark L. Yoslow, New York, all of N.Y.

[73] Assignee: Wilmark Electronic Co., Inc., New York, N.Y.

[22] Filed: Aug. 20, 1975

[21] Appl. No.: 606,170

Related U.S. Application Data

[62] Division of Ser. No. 392,489, Aug. 29, 1973, Pat. No. 3,908,279.

[52] U.S. Cl............................. 128/2 S; 33/174 D
[51] Int. Cl.²............................................. A61B 5/10
[58] Field of Search........ 128/2 S; 33/174 D, 174 L; 338/47

[56] References Cited
UNITED STATES PATENTS

| | | | |
|---|---|---|---|
| 2,508,419 | 5/1950 | Ramberg | 33/143 L |
| 3,520,294 | 7/1970 | Fuzzell et al. | 128/2 S |
| 3,608,541 | 9/1971 | Hall | 128/2 |
| 3,820,529 | 6/1974 | Gause et al. | 128/2 S |

FOREIGN PATENTS OR APPLICATIONS

| | | | |
|---|---|---|---|
| 231,711 | 9/1969 | U.S.S.R. | 128/2 S |

Primary Examiner—Kyle L. Howell
Attorney, Agent, or Firm—Friedman, Goodman & Teitelbaum

[57] ABSTRACT

A curvature measurement device is described having an elongated flexible member with at least one sensing wire attached at one end of the flexible member and extending along said flexible member to the other end thereof. The flexible member is attached to an object whose curvature is to be measured, such as the spine of a patient, and flexed in accordance with the shape of the object. A deviation sensing means coupled to the non-fixed end of the sensing wire measures the change in position of said wire as the flexible member is flexed to produce an electrical output signal proportional to the change in position.

3 Claims, 15 Drawing Figures

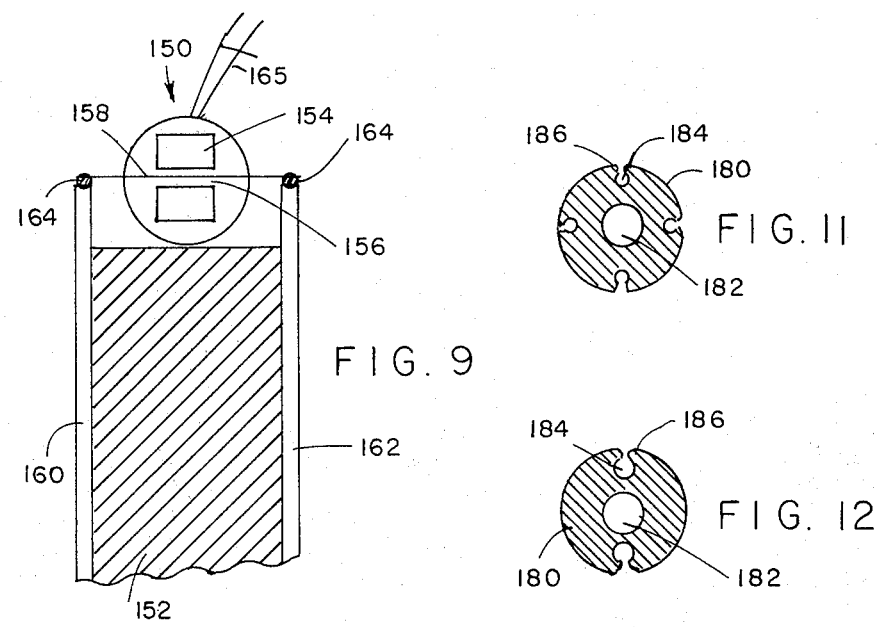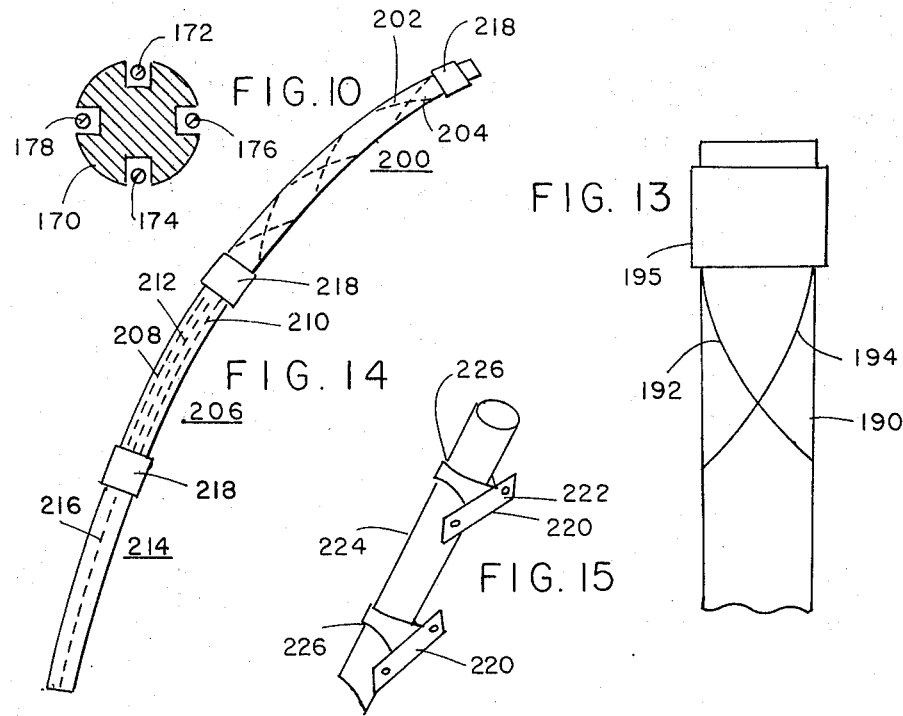

CURVATURE MEASUREMENT DEVICE

This is a division, of application Ser. No. 392,489 filed Aug. 29, 1973, now U.S. Pat. No. 3,908,279.

BACKGROUND OF THE INVENTION

This invention relates to a curvature measurement device, and more particularly to a device which can measure the continuous angular curvature or rotational curvature of an object. The invention has particular but not exclusive application to the measurement of the curvature of the human spine in connection with correct posture detectors.

In numerous fields of industry such as the construction industry or materials testing industry it is necessary to measure the curvature of a particular structural member, or to be able to continuously measure changes in curvature of such structural members. Most state of the art measurement devices for this purpose utilize strain gauges wherein a particular element such as a wire changes its dimension in accordance with changes in the curvature of the element to be measured. Some strain gauge devices utilize electrical resistance wires whose resistance changes as the dimensions of the wire change due to curvature of the object being measured. Other strain gauge devices utilize a wire in conjunction with a switch or other detecting element such that as the wire changes its dimensions in accordance with curvature of the element to be measured, the detecting device is triggered to produce an output signal.

While these devices may be satisfactory for some purposes, they generally are expensive and compplex because they require a special type of strain gauge element which is sufficiently sensitive to produce detectible results from even slight curvatures.

A specific application of such curvature measurement devices finds use in connection with poor posture detectors which are placed on the back of a wearer and detect spinal curvature. It is well known that malposition of the human spinal column is the cause of many ailments. Such ailments, as well as discomfort, can be avoided with correct posture; however, a patient is generally not aware of his poor posture position, By utilizing a curvature measurement device it is possible to provide the patient with greater spinal curvature awareness than he could achieve naturally.

One poor posture detector known in the art is described in U.S. Pat. No. 3,608,541. This device utilizes a flexible column hinged at one side thereof which has an actuating cable at the opposite side thereof which actuates a switch when the column is flexed greater than a given preset amount. While this device eliminates the necessity for a strain gauge detector, it cannot provide continuous signals proportional to any change in the curvature. In addition, because of its special construction, it is inherently limited in use to spinal curvature detection. Furthermore, the detector is limited to the use of one wire because of its peculiar construction. Still further, the detector described in the aforementioned patent can only detect angular curvature in a given plane but can not detect rotational curvature about a given axis.

SUMMARY OF THE INVENTION

It is therefore an object of this invention to provide a curvature measurement device which avoids the aforementioned problems of the prior art.

Still a further object of the invention is to provide a curvature measurement device which can provide a continuous electrical output signal proportional to curvature changes in an object being measured.

Still another object of this invention is to provide a curvature measurement device which can be utilized to measure angular curvature in a given plane and/or rotational curvature about a given axis.

Yet another object of this invention is to provide a curvature sensing device which senses curvature in an object being measured and provides signals to a deviation sensing device which produces an electrical signal proportional to said curvature changes.

A further object of this invention is to provide a curvature measurement device which can be used as a poor posture detector providing continuous output signals proportional to the changes in curvature of the spine.

Still another object of the invention is to provide a curvature measurement device which can be present to detect all changes in curvature from the preset position.

Still another object of the invention is to provide a curvature measurement device which is simple in construction and easy to utilize.

These and other objects, features and advantages of the invention will in part, be pointed out with particularity, and will in part become obvious from the following more detailed description of the invention taken in conjunction with the accompanying drawings, which forms an integral part thereof.

Briefly, this invention provides an elongated flexible member which can be coupled to an object whose curvature is to be measured, such as for example the spine of a patient. At least one sensing wire is fixedly connected to said flexible member at one location thereof, such as the base end of the elongated flexible member. The sensing wire extends along the flexible member to another location thereof, such as for example the opposite end of the elongated flexible member. As the flexible member flexes in accordance with a change in the curvature of the object to be measured, the sensing wire will change its position relative to the flexible member. A deviation sensing device located at the unconnected end of the sensing wire can detect the change in position of the sensing wire relative to the flexible member. Such change in position is converted into an electrical signal which will be proportional to the change in curvature.

In one embodiment of the invention two sensing wires are located on either side of the elongated flexible member forming a single plane which can detect curvature of the flexible member within that plane. By utilizing four wires in two pairs, two different planes can be established and curvature of the flexible member within each plane can be measured. By utilizing sensing wires which are spirally wound about the flexible member rotational curvature about a central axis can be measured.

In one embodiment the deviation sensing device is a resistive collar having a voltage impressed across it and being fixed to one end of the elongated flexible member. The sensing wires terminate in sliding means which can slide along the internal surface of the resistive collar. The voltage across the sensing wires is measured at the output. As the flexible member flexes, the position of the sliding means will change within the internal surface of the resistive collar thereby changing the voltage output across the two sensing wires.

In another embodiment the sensing wires are interconnected within an electrical bridge arrangement and the change in position of the wire changes the resistance of the bridge arms such that the amount of positional change in the wires can be measured.

BRIEF DESCRIPTION OF THE DRAWINGS

With the above and additional objects and advantages in view, as will hereinafter appear, this invention comprises the devices, combinations and arrangements of parts hereinafter described and illustrated in the accompanying drawings of a preferred embodiment in which:

FIG. 9 is a fragmentary sectional elevational view of yet another embodiment of the measuring device in accordance with the present invention;

FIG. 10, 11 and 12 are transverse sectional views showing various ways of retaining the wires to the flexible member in accordance with the present invention;

FIG. 13 is an elevational view of the sensing device wherein the wires are spirally located relative to the flexible member;

FIG. 14 is an elevational view of a cascaded assembly in accordance with the present invention; and FIG. 15 is an isometric view of retaining means useful in accordance with the measuring device of the present invention.

DESCRIPTION OF THE PREFERRED EMBODIMENTS

Figure 1:
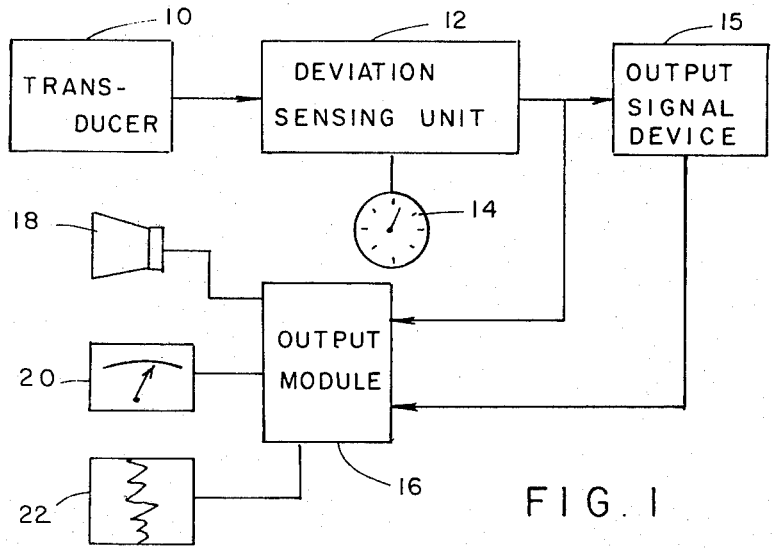
FIG. 1 is a block diagram showing the basic elements of the present invention as used in a complete measuring system.

Referring now to FIG. 1 there is shown a general block diagram of the curvature measurement device incorporated within a measurement system in accordance with the present invention. There is included an input transducer 10 which is fastened to the object whose curvature is to be measured, such as a patient's spine. The transducer can be fastened with conventional means such as tape, elastic belt, or in the case of industrial objects by means of brace devices or other known means. The transducer provides an output which is a function of the curvature of the object being measured.

A deviation sensing unit 12 receives the output signal from the transducer and calculates a deviation signal from a preset value. By adjustment of the preset value through means 14, a zero signal can be obtained at any desired curvature. As the transducer is flexed to a smaller radius of curvature, that is to say more bending of the object, the deviation signal becomes proportionately larger.

An output signal device 15 receives the deviation signal and produces the necessary conditioned output signal needed by the outputu module 16. The detailed circuitry of the output signal device 15 as well as the output module 16 will depend upon the type of output transducer used in connection with the present invention. By way of example, the output module can feed an audio system 18 wherein the tone, frequency or amplitude of the output audio signal is proportional to the deviation signal produced. A visual system 20 can be utilized wherein a meter has its output proportional to the deviation signal. Other types of visual systems could be used wherein the color, amplitude or spacial orientation is proportional to the deviation signal. The output module 16 could also feed into graphic devices 22 or computer devices where the output signal is registered in a computer memory for storage or further computational use.

When utilizing the curvature measurement device of the present invention as a poor posture detector, other types of output transducers could be used as well. For example, a skin stimulation system could be utilized wherein the frequency or amplitude of the stimulation to the wearer is proportional to the deviation signal. Also, a direct muscle stimulation system could be utilized wherein the stimulation is proportional to the deviation signal. Also, a pain stimulation system could be utilized where the amount of pain stimulation to the wearer is directly proportional to the deviation signal, which would then provide him with a reminder of the poor posture and encourage him to correct the spinal curvature thereby improving his posture.

Figure 2:
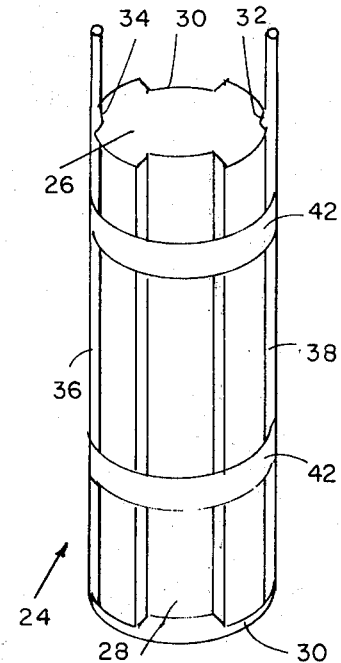
FIG. 2 is a frontal isometric view of one embodiment of the measuring device of the present invention.

Referring now to FIG. 2 there is shown a transducer, shown generally at 24 which includes a support member in the form of an elongated flexible member 26 which is shown provided with open longitudinal grooves 28, 30, 32 and 34 about the periphery of the member 26. The member 26 may be made from any suitable material which permits it to be flexed without breaking. An example of such material is nylon.

Although four grooves in the form of two pairs of opposite grooves have been shown, the present invention can also be used with less than four grooves, as will become apparent hereafter.

In the embodiment shown, grooves 32 and 34 are utilized in which respective sensing wires 36 and 38 are disposed. The wires are fixedly coupled to the flexible member at one location thereof. As can best be seen in FIG. 3, the wires 36 and 38 are joined at the bottom of the flexible member 26 by a connecting wire portion 40. The provision of the wire portion 40 is not critical and any other means of securing the wires 36 and 38 which prevents the wires from being completely separated from the flexible member could also be utilized. Retaining bands 42 enclose the flexible member 26 as well as the wires 36, 38 and prevent the latter wires from moving transversely outside the grooves. Therefore, although the wires 36, 38 may slide longitudinally within the grooves relative to the flexible member 26, when the latter flexes, as will be hereinafter described, the wires may not move outside the grooves. Consequently, the wires 36, 38 remain parallel to each other independently of the flexure of the member 26. The two parallel wires 36, 38, in the absence of twisting of the rod 26 about its own axis, always define a single plane.

Figures 3, 4:
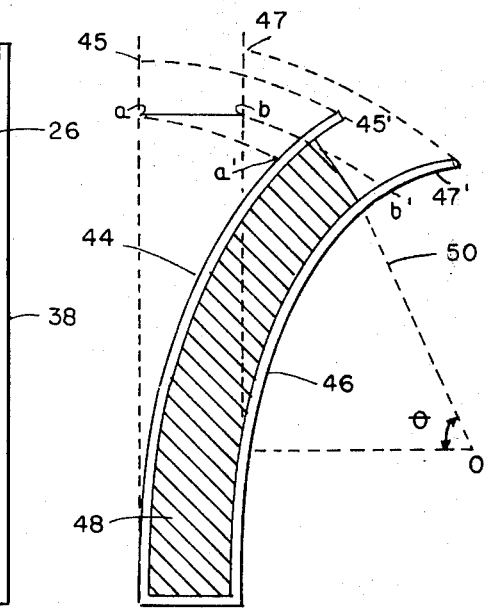
FIG. 3 is a sectional elevational view of the embodiment shown in FIG. 2.
FIG. 4 is a schematic diagram useful in explaining the theory of operation of the present invention.

In the embodiment shown in FIGS. 2 and 3 two parallel wires 36, 38 were utilized. It is understood that a single wire could also have been utilized to provide output results. In addition, all four grooves could be utilized wherein the wires 36, 38 shown would form one parallel pair lying in a first plane and additional wires would be placed within the grooves 28, 30 to form a second pair lying in a second plane. Although in the embodiment shown such two planes would be orthogonally related, such is not necessary and any intersecting planes could be used. Furthermore, although the wires in a given pair of grooves are shown interconnected by means of the section 40, each of the wires could independently be attached to the flexible member, and in fact, for some embodiments of the deviation sensing means, as will be hereinafter described, separate wires are required.

The principle of operation of the present invention can best be explained with reference to FIG. 4. When only two oppositely disposed wires 44, 46 are used, the curvature device or transducer is utilized to measure curvature in a plane defined by the two wires. In FIG. 4, the lower portion of the rod 48 is shown unflexed. An upper portion of the rod is shown flexed about a point 0. The wire 46 has a radius of curvature designated by the reference numeral 50 while the wire 44 has a radius of curvature which is equal to the radius of curvature 50 plus the cross sectional diameter of the rod 48. Consequently, within the curved arc defined by the angle $\theta$, the length of the wire 46 within the curved arc is smaller than the length of the wire 44 enclosed by the same curved arc. Accordingly, the extension 47' relative to the rod 48 increases over the initial length of the extension 47 while the length of the extension 45' decreases in relation to its original length of extension 45. Thus, as shown, a given point on wire 44 which, in its original position coincided with the upper end of the flexible rod 48 now represents a point $a'$ which is further down along the flexible member 48. Similarly, a point $b$ which in its original position coincided with the upper end of the flexible member 48, when flexed, now becomes $b'$ which is a distance beyond the end of the flexible member 48. Flexing towards the left instead of the right would increase the length of the extension 45' while decreasing the length of the extension 47' in relation to the original length when the rod is unflexed.

The change of lengths of the extensions relative to the flexible member, contains information relating to the curvature which the member experiences. Thus, one wire could also be used to sense the curvature change. Two wires, identifying a single plane, senses curvature within that single plane. However, the use of two wires presents a greater measureable deviation from the unflexed condition which can provide greater sensitivity of measurement.

Figure 5:
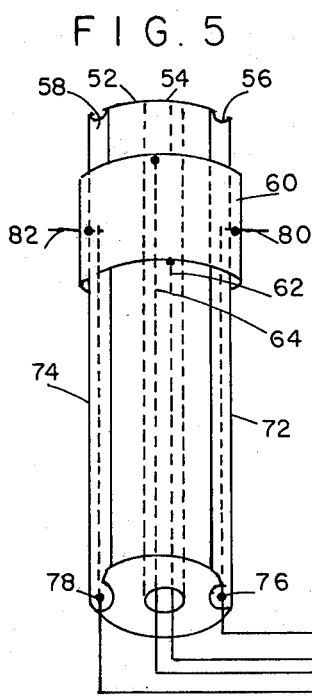
FIG. 5 is a frontal isometric and partly electrical schematic drawing of another embodiment of the present invention.
Figure 6:
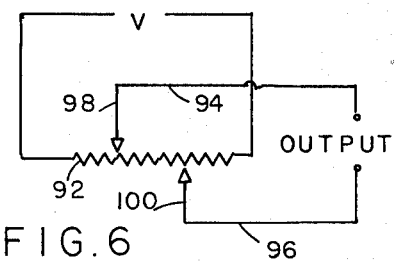
FIG. 6 is an electrical schematic drawing showing the equivalent of the device of FIG. 5.

Once the sensing transducer detects a change in curvature by means of the relative change in position of the unfixed end of the sensing wires, this change in position is then translated into continuous electrical signals which are proportional to such change in position. Referring now to FIGS. 5 and 6 one such deviation sensing means for producing an electrical output proportional to such positional change in sensing wires is shown. In this embodiment a non-conductive elongated flexible member 52 in the form of a cylindrical tube has a hallowed central bore therein with longitudinal grooves 56, 58 on opposing outer sides thereof. A resistive collar 60 is mounted adjacent one end of the flexible member member and anchored fixedly to the flexible member. Opposite edges of the resistive collar are connected respectively to wires 62 and 64 which pass through the central bore 54 and lead from the flexible member such that terminals 66, 68 are available across which a voltage supply 70 can be connected.

Conducting sensing wires 72, 74 are located within the grooves and fixed to the flexible member at points 76, 78. The upper ends of each of the wires 72, 74 connect to conductive sliders 80, 82 which reside in the groove of the core and abut the inner surface of the collar 60. The ends of the wire opposite from that of the sliders are available externally at the output terminals 84, 86. A measuring device, such as a volt meter 88 can be interconnected across the output terminals 84, 86 to measure the voltage across the conducting sensing wires 72, 74. A variable resistance 90 can be placed across the volt meter 88 to zero the volt meter 88 at any specific value thereby presetting a reference zero voltage corresponding to a given referenced amount of curvature.

Referring now to FIG. 6 there is shown an electrical equivalent of the embodiment shown in FIG. 5. It is seen that a voltage V is impressed across a resistor 92. The resistor 92 represents the resistive collar 60 in FIG. 5. Wires 94 and 96 correspond to the longitudinally extending sensing wires 72, 74 in the embodiment of FIG. 5. The ends of these wires are respectively connected to sliders 98, 100 which abut the resistance 92. As the sliders 98, 100 are caused to move apart, a different amount of voltage can be sensed at the output terminals between the wires 94, 96. The amount of voltage is proportional to the amount of spacing between the sliders 98, 100. Normally, zero voltage would be read when the slider 98 is located at the same point on the resistor 92 as the slider 100. A maximum voltage will exist when the slider 98 is at one end of teh resistor 92 and the slider 100 is at the opposing end. Any intermediate values will be proportional to the amount of distance the slider arms are moved relative to the resistor 92. The output can be read by a volt meter and the volt meter can be zero adjusted such that for a given distance between the sliders 98 and 100 the voltage will read zero and will subsequently read positive or negative voltage values relative to that predetermined referenced zero position. Thus, a given amount of curvature can be established as the reference point and all curvatures greater or lesser than the reference amount can be read out.

Figure 8:
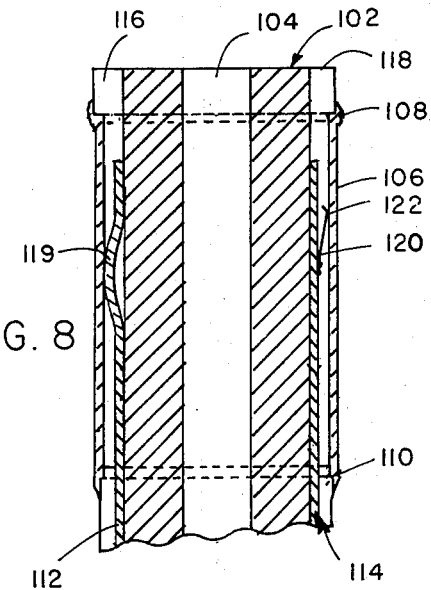
FIG. 8 is a fragmentary sectional elevational view of the embodiment shown in FIG. 5.

Referring now to FIG. 8 there is shown various methods of interconnecting the ends of the sensing wires to the resistive collar. In FIG. 8, the non-conductive flexible member 102 contains the central bore 104 and a resistive collar 106 which has conductive bands 108, 110 which can respectively be interconnected across the voltage source through wires contacting the same (not shown). The conductive wires 112, 114 pass through grooves 116, 118 respectively, such that they contact the inner surface of the resistive collar 106. In one method shown in conjunction with wire 112 a curved portion 119 is formed in the wire and made rigid such that it abuts the inner surface of the resistive collar 106 and can slide along each inner surface. In another method, shown in conjunction with conductive wire 114 a leaf spring 120 of conductive material is fixedly connected onto the conductive wire 114 and has the outer edge thereof 122 slidably brushing against the inner surface of the resistive collar 106. In either method, the slide means will be in contact with the inner surface of the resistive collar and the position of the slide means will vary as the curvature of the flexible member 102 changes in the plane formed by the wires 112, 114.

Figure 7:
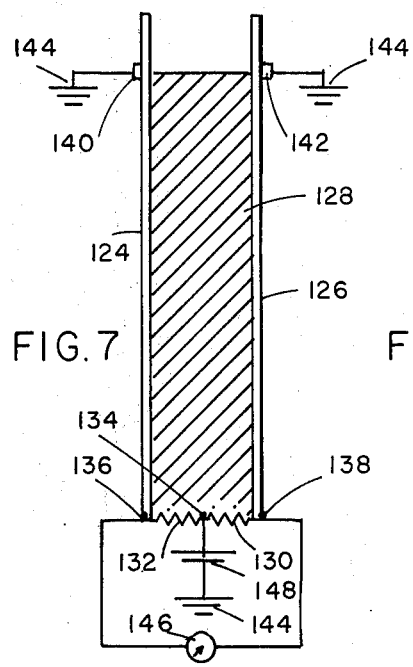
FIG. 7 is a sectional elevational and partly electrically schematic drawing showing a further embodiment of the measuring device in accordance with the present invention.

An alternate approach to providing a deviation sensing means is shown in FIG. 7 wherein resistive wires 124, 126 are utilized. The lower ends of these wires are connected to the bottom of the flexible member 128 in any conventional manner. An electrical bridge arrangement is utilized having fixed resistors 130 and 132 forming two arms with a terminal point 134 therebetween. Resistive wire 124 is connected at terminal point 136 to resistor 132 and similarly resistive wire 126 is connected at terminal point 138 to resistor 130. Brush slides 140, 142 are respectively connected at the ends of the conductive wires 124, 126 to detect change in position of the wires as the flexible member is flexed. The ends of the brush slides are connected to ground at 144, which forms the fourth terminal of the bridge. A voltage source 148 is interconnected across two opposing terminals 134 and the ground terminal 144. An indicator means 146 is connected across the other opposing diagonal terminals 136, 138. In this manner the resistive wire 124 in conjunction with the brush 140 forms one arm of the bridge and the resistive wire 126 in conjunction with the brush 142 forms the other arm of the bridge. The resistance of each of these arms will change as the flexible member is flexed. Such change in resistance unbalances the bridge which unbalance can be read on the indicator 146 whose output will be a functional relationship with the amount of curvature caused by the flexure of the flexible member 128.

Still another approach to detecting the deviation in position of the sensing wires and coverting it to an electrical signal is shown in FIG. 9. In this embodiment a potentiometer 150 is mounted on top of the flexible member 152. The potentiometer 150 has a screwhead 154 with a slot or groove 156. Such potentiometers are available and utilized in printed circuits. The potentiometer adjustment is made by inserting a screwdriver into the slot 156 and turning the head 154 in one direction or another about the axis of the potentiometer 150. When used with the present invention, a fixed connector 158, such as a wire may be connected to the ends of the sensing wires 160, 162 by any suitable means such as for example solder or welds 164. The wire 158 is made to pass through the slot 156. Electrical leads 165 of the potentiometer 150 are connected to a suitable circuit such as an oscillator or bridge circuit. When the wires 160, 162 change in length, the wire 158 is caused to turn about the axis of the potentiometer 150 and head 154 is similarly caused to turn. The null position or normal position of thhe head 154 is shown in FIG. 9. It is to be noted, that in this embodiment the sensing wires which extend along the flexible member need not be made of electrically conductive material. Thus, it would be possible to use an interconnecting wire to fixedly connect the sensing wires to the elongated flexible member as was described in connection with FIG. 3.

In FIG. 10, the curvature sensing device is shown with four wires contained in four grooves within the flexible member 170. Wires 172 and 174 define a first plane which will detect curvature movement within that plane. Wires 176 and 178 define a second plane and will detect curvature within that plane. Although the planes are shown orthogonally perpendicular they can be intersecting at other angles as was heretofore explained. In addition, arbitrary bending of the rod 170 in other planes causes all four wires to change in length. By knowing the components of curvature in each of the two major planes, the resulting curvaturre in any other plane may be ascertained.

Referring now to FIGS. 11 and 12 there is shown the flexible member 180 having the center bore 182 and wherein the grooves 184 are formed with a narrow neck portion 186 at the outer surface. The necks are formed such that they can slightly deform and spread apart upon application of pressure. When inserting the wires, such pressure is placed at the narrow neck portion to deform it, thereby permitting the wires to enter therein. Once the wires are placed within the grooves they are retained by the narrow neck and no additional retaining means need be connected to hold the wires within the grooves. FIG. 11 shows an embodiment having four wires while FIG. 12 shows an embodiment containing two wires.

Although heretofore the embodiments have shown the sensing wires extending longitudinally along the flexible member referring now to FIG. 13 there is shown an elongated flexible member 190 containing wires 192 and wires 194 spirally winding about the elongated flexible member. While one wire could be used, similar to using one wire in the longitudinal embodiment, two wires are shown wherein one is spirally rotated in a clockwise direction and the other is spirally rotated in a counterclockwise direction using two wires will increase the sensitivity of the device. As is shown, a resistive collar 195 is again used to sense the deviation and convert it to electrical signals. Using the spiral embodiment, the sensing device will possess rotational sensitivity and be able to continuously sense the rotational curvature about a center axis of the flexible member 190. The sensitivity of the unit will be inversely proportional to the pitch angle of the spiral.

By combining various individual sensing units it is possible to form a cascaded measurement sensor of the type shown in FIG. 14 wherein a first section shown generally at 200 contains rotational sensitivity by having spirally wound wires 202, 204 about the flexible member. The second section shown generally at 206 has dual axis sensitivity by including a first pair of wires 208, 210 extending longitudinally in a first plane and a second pair of wires one of which is shown 212 also extending longitudinally and lying in a plane perpendicular to the first pair. A third section shown generally at 214 contains single axis sensitivity by having a single pair of wires 216 extending longitudinally along the flexible member and lying in a single plane. Resistive collars 218 are used to sensed the deviation of each of the wires as was heretofore explained.

In order to utilize the present device either for industrial use on construction elements or material testing elements, or in order to provide use as a poor posture detector it is necessary to mount the flexible member onto the item being measured. When used as a poor posture detector, belt means can be utilized which secures the sensing device against the patient's spine.

Preferably, the belt means are easily secured around the patient and readily removed therefrom so that the patient can make necessary adjustments himself. The deviation sensing means could in fact be included within the belt and batteries utilized to supply the necessary voltage source to make the entire unit portable.

When attaching the curvature sensing device onto an industrial element brackets of the form shown in FIG. 15 at 220 could be utilized. Such brackets would include mounting holes 222 to firmly attach the flexible member 224 to the element being measured. However, the bands 226 should necessarily permit the member 224 to freely pass therein permitting flexure of the member 224 as the element bends and produces a given curvature.

There has been disclosed heretofore the best embodiments of the invention presently contemplated. However, it is understood that various changes and modifications may be made thereto without departing from the spirit of the invention.

What is claimed is:

1. A device for measuring curvature of a spine comprising an elongated flexible member, at least one pair of substantially parallel sensing wires extending longitudinally along said flexible member, the wires of said at least one pair being disposed on opposing sides of said flexible member and together defining a plane, said flexible member including retaining means for maintaining said wires substantially coextensive with said flexible member along lengths thereof and each of said wires of said at least one pair being fixedly connected at one end thereof to said flexible member and having an opposite end thereof free for longitudinally displacement along said flexible member within said plane, where flexing of said flexible member within said plane causes the free ends of said at least one pair of sensing wires to be displaced relative to each other in opposing directions along said flexible member; deviation means coupled to said free ends for producing an electrical signal proportional to a change of relative longitudinal positions of said free ends of a respective pair of sensing wires to thereby provide a measure of curvature within the respective plane; and attaching means connected to said flexible member for mounting said flexible member on the back of a wearer, said attaching means permitting flexure of said flexible member.

2. A device as in claim 1 and wherein said deviation sensing means comprises resistive collar means fixedly located on said member at said other location and adapted to have a voltage impressed across it, and wherein said sensing wires are conductive and include sliding means electrically contacting said resistive means whereby said electrical signal is the voltage between said wires.

3. A device for measuring curvature of a spine comprising an elongated flexible member; two sensing wires spirally extending along said flexible member in opposing rotational directions, said flexible member including retaining means for maintaining said wires substantially coextensive with said flexible member along lengths thereof and each of said wires being fixedly connected at one end thereof to said flexible member and having an opposite end thereof free for substantially axial displacement along said flexible member, where rotational flexing of said flexible member about a central axis thereof causes the free ends of said sensing wires to be displaced relative to each other along said flexible member; deviation means coupled to said free ends for producing an electrical signal proportional to a change of relative positions of said free ends of said pair of sensing wires to thereby provide a measure of rotational curvature about the central axis of said flexible member; and attaching means connected to said flexible member for mounting said flexible member on the back of a wearer, said attaching means permitting rotational flexure of said flexible member.

* * * * *